United States Patent
Poessel et al.

(10) Patent No.: US 9,820,485 B2
(45) Date of Patent: Nov. 21, 2017

(54) PHYTOSANITARY COMPOSITION

(71) Applicant: INSTITUT NATIONAL DE LA RECHERCHE AGRONOMIQUE-INRA, Paris (FR)

(72) Inventors: Jean-Luc Poessel, Le Thor (FR); Marie-Helene Sauge-Collet, Saint-Saturnin les Avignon (FR); Yvan Rahbe, Villeurbanne (FR)

(73) Assignee: INSTITUT NATIONAL DE LA RECHERCHE AGRONOMIQUE-INRA, Paris (FR)

( * ) Notice: Subject to any disclaimer, the term of this patent is extended or adjusted under 35 U.S.C. 154(b) by 0 days.

(21) Appl. No.: 15/119,252

(22) PCT Filed: Feb. 12, 2015

(86) PCT No.: PCT/FR2015/050346
§ 371 (c)(1),
(2) Date: Aug. 16, 2016

(87) PCT Pub. No.: WO2015/124846
PCT Pub. Date: Aug. 27, 2015

(65) Prior Publication Data
US 2017/0006866 A1    Jan. 12, 2017

(30) Foreign Application Priority Data
Feb. 19, 2014 (FR) ..................... 14 51341

(51) Int. Cl.
*A01N 37/38* (2006.01)
*A01N 37/46* (2006.01)
*A01N 43/16* (2006.01)

(52) U.S. Cl.
CPC ............. *A01N 37/38* (2013.01); *A01N 37/46* (2013.01); *A01N 43/16* (2013.01)

(58) Field of Classification Search
IPC .................................................... A01N 37/38
See application file for complete search history.

(56) References Cited

U.S. PATENT DOCUMENTS 8,921,420 B2 * 12/2014 Poessel .................. A01N 37/38
                                                      514/533
2011/0015140 A1    1/2011 Andary et al.
2011/0054022 A1    3/2011 Poessel et al.

FOREIGN PATENT DOCUMENTS

| EP | 1671534 A1 * | 6/2006 |
| FR | 2 904 935 A1 | 2/2008 |
| WO | 00/63152 A1 | 10/2000 |
| WO | 03/029183 A1 | 4/2003 |
| WO | 2008/022974 A2 | 2/2008 |
| WO | 2009/095624 A2 | 8/2009 |
| WO | 2012/000960 A1 | 1/2012 |

OTHER PUBLICATIONS

Beninger, C W, et al: "A Flavanone and Two Phenolic Acids From Chrysanthemum morifolium With Phytotoxic and Insect Growth Regulating Activity", vol. 30, No. 3, Mar. 1, 2004 (Mar. 1, 2004), pp. 589-606, XP007905930, ISSN: 0098-0331, Retrieved from the Internet <URL:http://www.springerlink.com/content/m361351564t278gq/fulltext.pdf> DOI: 10.1023/B:JOEC.0000018631.67394.E5.

Lukasik, I: "Changes in activity of superoxide dismutase and catalase within cereal aphids in response to plant o-dihydroxyphenols", vol. 131, No. 3, Jan. 1, 2007 (Jan. 1, 2007), pp. 209-214, XP007905925, Retrieved from the Internet <URL:http://www3.interscience.wiley.com/cgi-bin/fulltext/118521826/PDFSTART> DOI: 10.1111/J.1439-0418.2006.01136.X.

Kimmins, F M, et al: "Growth inhibition of the cotton bollworm (*Helicoverpa armigera*) larvae by caffeoylquinic acids from the wild groundnut, Arachis paraguariensis", Database CAPLUS, [online] Jan. 1, 1995 (Jan. 1, 1995), XP002499216, retrieved from CAPLUS Database accession No. 1998-97273.

International Search Report, dated Apr. 16, 2015, from corresponding PCT Application.

* cited by examiner

*Primary Examiner* — Shirley V Gembeh
(74) *Attorney, Agent, or Firm* — Young & Thompson

(57) ABSTRACT

The use of a polyhydroxylated polyaromatic compound, in particular of chicoric acid, for combating plant pests and phytosanitary composition comprising chicoric acid.

12 Claims, 3 Drawing Sheets

1A
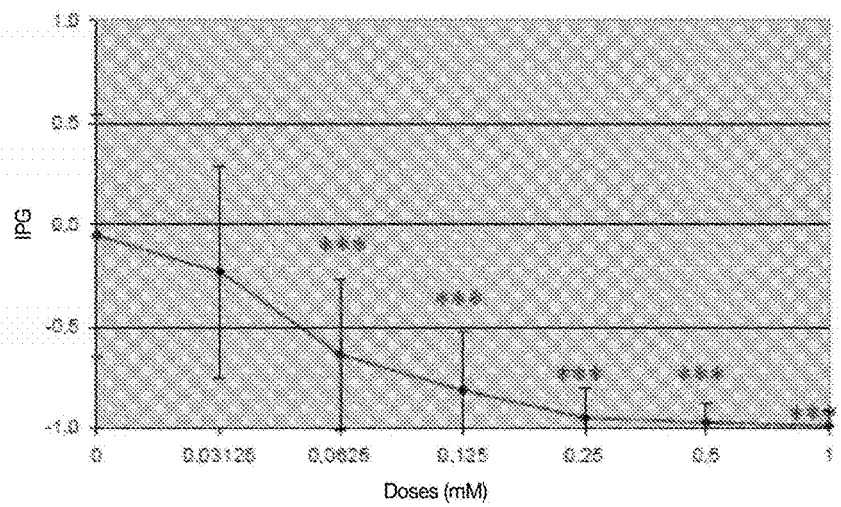
1B
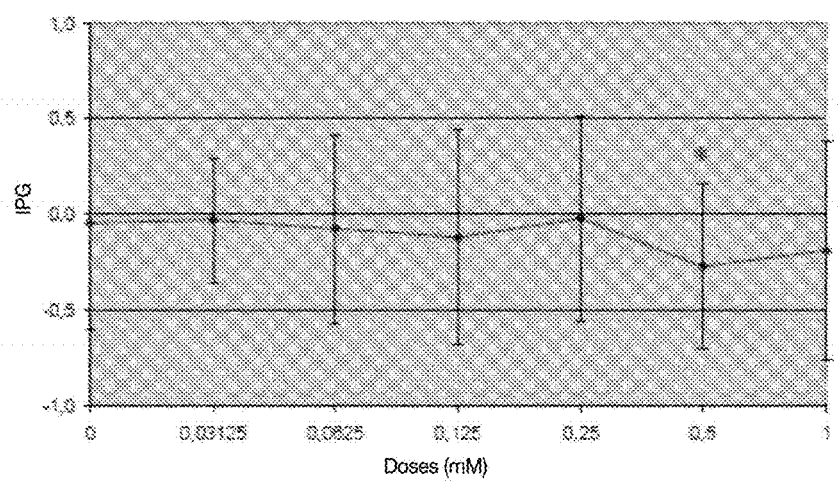

2A

2B

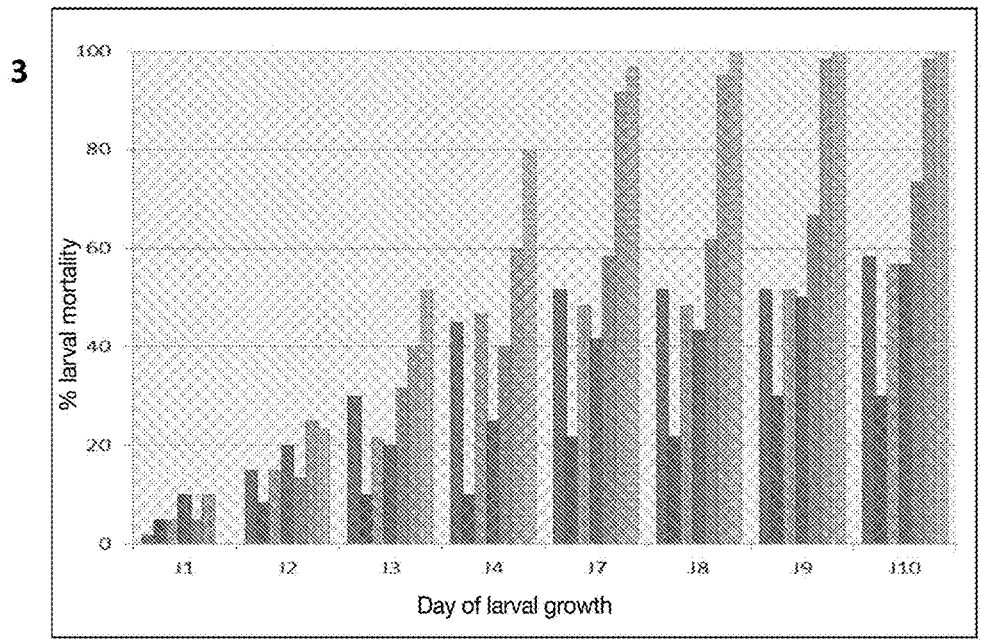

PHYTOSANITARY COMPOSITION

FIELD OF THE INVENTION

The present invention relates to the phytosanitary field and notably to the field of plant pest insect control. It particularly relates to compounds intended for phytosanitary applications along with the compositions containing same. Finally, it relates to a method for aphid control.

PRIOR ART

Plant pest insects, and notably phytophagous insects, cause economically significant damage in arable (fled) crops and horticultural crops and significantly reduce agricultural yields and diminish the harvests thereof if not eradicated. Indeed, pest insects feed on various parts of plants: leaves, flowers, roots, fruit, seeds, sap, etc. and cause damage which is usually very visible. Some phytophagous insects have crushing mouthparts, such as crickets, Colorado beetles or caterpillars, and can eat up leaves or other parts of plants. Other phytophagous insects, known as piercing-sucking insects, have sucking mouthparts, notably aphids, whiteflies, psylla and cochineals. These insects ingest plant sap by inserting their mouthparts therein (into the stalk, leaf or roots for example).

Of these piercing-sucking insects, aphids, due to the rate of development and spreading potential thereof, represent a genuine plague in agriculture. They attack almost all plant species. The damage can be seen in the form of yellowish mottled discolorations which normally appear on the underside of leaves which subsequently dry out and die. Some aphid species form galls or cause leaves to coil or become deformed. Aphids established on other parts of the plant, such as stalks or branches, may delay growth, cause rapid leaf loss or branch death. Aphids are also carriers of numerous viral diseases (CAB International (1996). Crop Protection Compendium—Global module, ($2^{nd}$ Edition). Other piercing-sucking insects, such as cochineals (for example *Planococcus citri*), whiteflies (for example *Trialeurodes vaporariorum, Bemisia tabaci*) or *psylla* (for example *Psylla pyri*) also cause significant damage in arable crops and horticultural crops.

Mention will particularly be made of the green peach aphid (*Myzus persicae*). The direct damage caused by this aphid on the primary host thereof, the peach tree, is caused by the feeding bites thereof causing buds to dry out, flowers to fall, foliage and shoots to become deformed, impede growth and may cause necrotic reactions (Massonié et al., (1979) revue de zoologie agricole et pathologie végétale 78, 1-5; Monet and Massonié, (1994) Agronomie 2 177-182; Monet and Guye, (1998) in Monet R. (Ed) Proc. Fourth Intern. Peach Symposium Acta Hort 171-175). This piercing-sucking insect is particularly harmful for the peach tree, as it is a potential carrier of Plum Pox Virus, the causal agent of Sharka disease, which causes deformations and discolorations of fruit rendering said fruit unfit for sale. As no curative control means for this virus is available, infected trees must be removed. *Myzus persicae* finds a secondary host in numerous herbaceous plants of which some have a major economic importance: potato, cabbage, rapeseed, eggplant, beetroot, tomato, bell pepper, etc. This aphid is very harmful for these crops due to the direct damage caused thereby and the transmission of numerous viruses caused thereby.

Numerous insecticides are known for controlling pest insects; however, residues of these chemical compounds are found in the environment; they affect biodiversity, contaminate foodstuffs and have a negative impact on human health.

Insecticides of natural origin and notably of plant origin have thus been developed having a lower toxicity for humans and the environment. Compositions based on pyrethrum or geraniol are thus known, for example.

Recently phytosanitary products intended for aphid control comprising quinic acid derivatives were proposed (WO2009/095624).

Chicoric acid is known for the cosmetic or pharmacological applications thereof, notably as an anti-viral compound (WO200063152), as a depigmenting agent (WO2012000960), or for treating disorders associated with metabolic syndrome, such as hyperinsulinemia, hypertriglyceridemia, pre-diabetes, overweight (WO2008022974).

Applications for treating HIV have also been proposed (Robinson et al., PNAS 1996, 93:6326-31).

A study by Snook et al. (J. Agric. Fodd Chem., 1994, 42:1572-74) revealed the presence of chicoric acid in some peanut varieties exhibiting resistance to *cercosporidium personatum* fungus, tobacco thrips (*cercosporidium personatum*), or the potato leafhopper (*empoasca fabae*). Nevertheless, the chicoric acid contents found are not correlated with the degree of resistance of peanut plants to these organisms.

As such, to the inventors' knowledge, chicoric acid or any of the derivatives thereof has never been previously proposed for phytosanitary applications, notably for controlling insects of the aphid and phylloxeroidea superfamily.

Besides the toxic effects thereof, in respect of the environment and/or human or animal health, the use of insecticides, which is very widespread, progressively leads to the selection of resistant subjects for which eradication becomes increasingly difficult.

It is thus necessary to have new compounds which are effective against pest insects, notably against aphids, at the lowest possible doses.

It is also desirable to have compounds having an enhanced efficacy/efficiency (higher than the one of the compounds according to the prior art), easy to formulate and non-toxic.

SUMMARY OF THE INVENTION

The present invention meets this need since the inventors discovered that a compound having formula (I), chicoric acid (also known as dicaffeyl tartaric acid) has a strong insecticidal, and notably aphicidal, potential, while being devoid according to current knowledge of harmful effects for the environment and human health. Furthermore, this compound has a very low effective dose, suitable for repelling or eliminating pest insects.

The present invention thus relates to the use of a compound having formula (I):

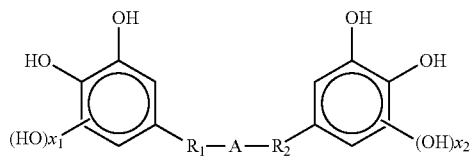

wherein, $x_1$ and $x_2$ are each independently=0 or 1;

—$R_1$— represents a group chosen from

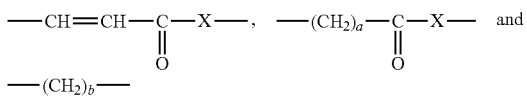

—$R_2$— represents a group chosen from

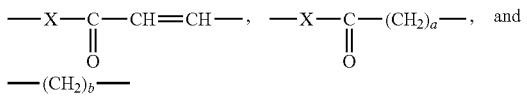

wherein for —$R_1$— and —$R_2$—:
—X— represents O or N,
a=0, 1, or 2
b=1, 2 or 3, and preferably b=1 or 2;
-A- represents a mono-saccharide, a di-saccharide or a group chosen from:

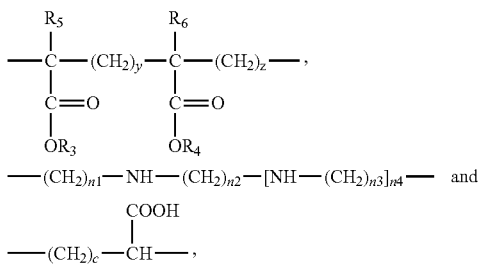

wherein
y and z are each independently equal to 0, 1, 2, 3 or 4
—$R_3$ and —$R_4$ each represent independently H or a $C_1$-$C_3$ alkyl
$n_1$, $n_2$, $n_3$ are each independently equal to 1, 2, 3, or 4 and $n_4$=0 or 1
c=2, 3 or 4, preferably 3;
$R_5$— and $R_6$— each represent independently H, OH or the group

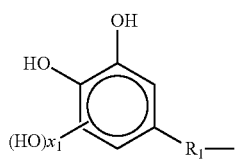

where —$R_1$— chosen between

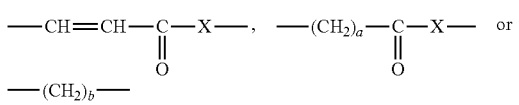

where b=1, 2 or 3, and preferably b=1 or 2;
for controlling plant pests, particularly insects of the Aphidoidea and Phylloxeroidea superfamily.

The present invention also relates to a phytosanitary composition comprising at least one compound having formula (I), notably chicoric acid, in a concentration ranging from 0.06 to 5 mM and preferably at least one excipient suitable for phytosanitary uses.

Finally, the present invention also relates to a phytosanitary treatment method and notably for controlling aphids, comprising a step consisting of applying at least one compound having formula (I) or a composition containing same onto aphids, at a site infested with aphids or at a site liable to be infested by aphids.

DESCRIPTION OF THE FIGURES

FIG. 1. Comparison of the phagorepellent effects of chicoric acid (dicaffeyl tartaric acid) and caftaric acid (monocaffeyl tartaric acid) on *Myzus persicae* aphids: phagostimulation index (IPG) as a function of the dose of chicoric acid (1A) or caftaric acid (1B) at doses ranging from 0 mM to 1 mM (0; 0.03125; 0.0625; 0.125; 0.25; 0.5 and 1 mM).

FIG. 2. Cumulative daily mortality observed during *Myzus persicae* larval growth: Histogram illustrating the percentage of larval mortality of *Myzus persicae* aphids from the first (D1) to the seventh day (D7) (from left to right), for doses ranging from 0 to 1 mM (0.03125; 0.0625; 0.125; 0.25; 0.5 and 1 mM) of chicoric acid (2A) or caftaric acid (2B).

FIG. 3: Cumulative daily mortality observed during *Acyrthosiphon pisum* larval growth. Histogram illustrating the percentage of larval mortality of *Acyrthosiphon pisum* aphids from the first (D1) to the tenth day (D10) of the larval growth thereof, for doses of chicoric acid of 0; 0.03125; 0.0625; 0.125; 0.25; 0.5 and 1 mM (from left to right for each day of larval growth).

DETAILED DESCRIPTION

The present invention relates to the use, for controlling plant pests, of at least one compound having formula (I):

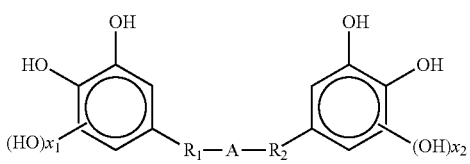

wherein,
$x_1$ and $x_2$ are each independently=0 or 1;
—$R_1$— represents a group chosen from

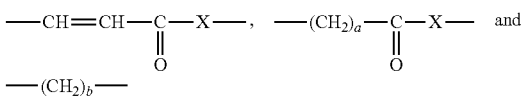

—$R_2$— represents a group chosen from

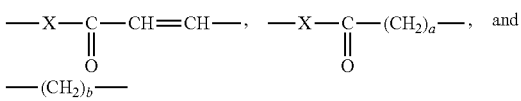

wherein for —R$_1$— and —R$_2$—:
—X— represents O or N,
a=0, 1, or 2
b=1, 2 or 3, and preferably b=1 or 2;
-A- represents a mono-saccharide, a di-saccharide or a group chosen from:

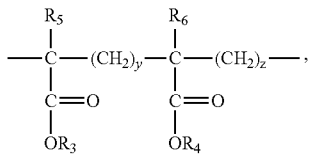

—(CH$_2$)$_{n1}$—NH—(CH$_2$)$_{n2}$—[NH—(CH$_2$)$_{n3}$]$_{n4}$— and

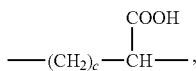

wherein
y and z are each independently equal to 0, 1, 2, 3 or 4
c=2, 3, or 4, preferably 3;
n$_1$, n$_2$, n$_3$ are each independently equal to 1, 2, 3, or 4 and n$_4$=0 or 1
R$_3$ and R$_4$ each represent independently H or a C$_1$-C$_3$ alkyl
R$_5$— and R$_6$— each represent independently H, OH or the group

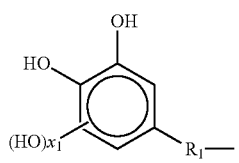

where —R$_1$— is chosen between

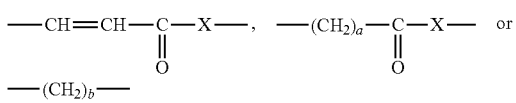

where b=1, 2 or 3, and preferably b=1 or 2;
for controlling plant pests.
Unless specified otherwise, the various embodiments of a compound having formula (I) according to the invention described hereinafter may be taken alone or in combination:
A monosaccharide or simple sugar is a carbohydrate monomer. It has 3 to 9 carbon atoms, preferably 3 to 6 and particularly preferably 4 to 6 carbon atoms. According to the invention it may consist of a poly hydroxy aldehyde (aldose) or a poly hydroxy ketone (ketose). In one particular embodiment of the invention, the group -A- as defined above is glucose.
In some embodiments, —R$_1$— represents a group chosen from:

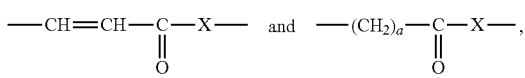

wherein —X— represents O or N, and preferably O, and a=0, 1, or 2 and preferably 0 or 1 and notably a=0, and and —R$_2$— represents a group chosen from:

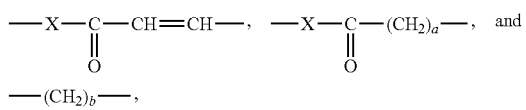

wherein —X— represents O or N, and preferably O, and a=0, 1, or 2 and preferably 0 or 1 and notably a=0.
Preferably, in a compound having formula (I)

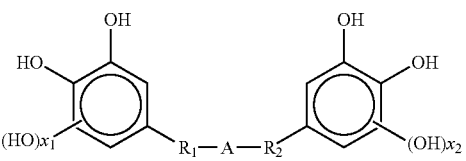

according to the invention, when the group —R$_1$— and/or —R$_2$— represent(s) respectively a group chosen from the groups consisting respectively of

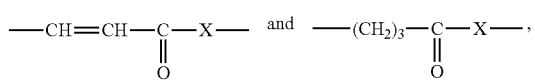

for —R$_1$— and

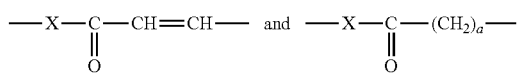

for —R$_2$—, then x$_1$ and/or x$_2$=0. More preferably, —X— represents O.
Also preferably, in a compound having formula (I) according to the invention, R$_5$— and R$_6$— each represent independently from one another H or OH.
Also in some embodiments, -A- preferably represents the group

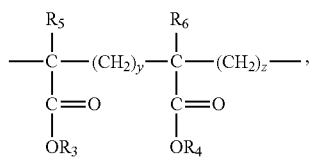

wherein:
y and z are each independently equal to 0, 1, 2, 3 or 4, preferably y and z are each independently equal to 0 or 1 and notably equal to 0
R$_3$ and R$_4$ each represent independently H or a C$_1$-C$_3$ alkyl, preferably a C1 alkyl, more preferably R$_3$ and R$_4$ each represent H
R$_5$ and R$_6$ each representing independently H or OH, and preferably H
Preferably, in these embodiments, —R$_1$— and —R$_2$— represent(s) respectively a group chosen from the groups consisting of respectively

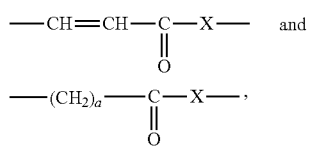

for —$R_1$— and

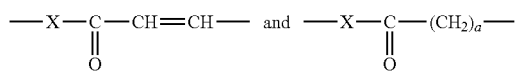

for —$R_2$—, wherein:
—X— represents O or N, and preferably O
a=0, 1, or 2, notably 0 or 1 and preferably 0
More preferably in these embodiments, $R_1$ and $R_2$ each represent respectively the group

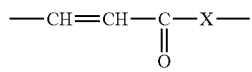

for $R_1$ and

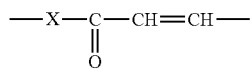

for $R_2$.

In one preferred compound having formula (I) according to the invention:
—$R_1$— and —$R_2$— each represent respectively a group chosen from

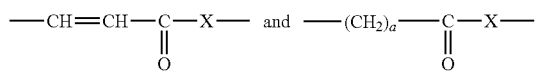

for —$R_1$— and a group chosen from

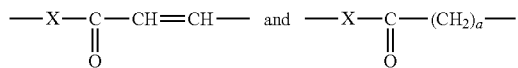

for —$R_2$—, wherein —X— represents O and a=1 or 2; and -A- represents the group

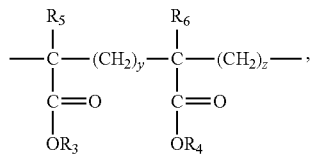

wherein y and z are each equal to 0 or 1, and $R_3$, $R_4$, $R_5$ and $R_6$ are each H.

In some embodiments, in a compound having formula (I) above, when -A- represents the group —$(CH_2)_{n1}$—NH—$(CH_2)_{n2}$—[NH—$(CH_2)_{n3}]_{n4}$—, $n_1$ is preferably equal to 3, $n_2$ is preferably equal to 4, $n_4$ is equal to 0 or 1. When $n_4$ is equal to 1, $n_3$ is preferably equal to 3. In such an embodiment, —$R_1$— and —$R_2$— preferably each represent respectively a group chosen from:

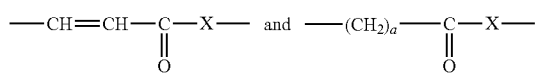

for —$R_1$— and a group chosen from

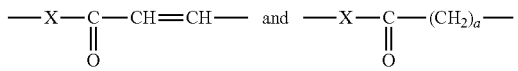

for —$R_2$—, wherein:
—X— represents O or N, and preferably N
a=0, 1, or 2

In one preferred compound having formula (I) according to the invention:
—$R_1$— and —$R_2$— each represent respectively a group chosen from

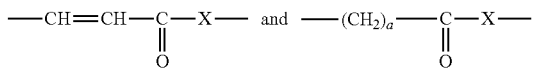

for —$R_1$— and from

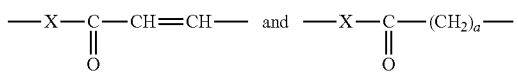

for —$R_2$—, wherein —X— represents N and a=1 or 2; and
-A- represents the group —$(CH_2)_{n1}$—NH—$(CH_2)_{n2}$—[NH—$(CH_2)_{n3}]_{n4}$—, wherein $n_1$, $n_2$, $n_3$ are each independently equal to 1, 2, 3, or 4 and $n_4$=0 or 1.

According to one preferred embodiment of the invention, the groups —$R_1$— and —$R_2$— of a compound having formula (I) each represent respectively a group chosen from

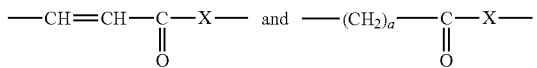

for —$R_1$— and from

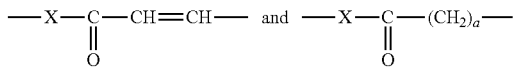

for —$R_2$—. Preferably, the groups —$R_1$— and —$R_2$— of a compound having formula (I) are identical.

Examples of compounds having formula (I) suitable for the invention are notably:
dicaffeyl tartaric acid (or chicoric acid), having the formula:

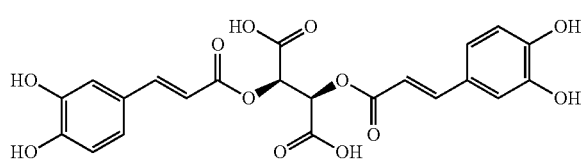 [SMILES: O=C(/C=C/c1ccc(O)c(O)c1)O[C@@H](C(=O)O)[C@@H](OC(=O)/C=C/c1ccc(O)c(O)c1)C(=O)O]

Dicaffeylspermidine, having the formula:

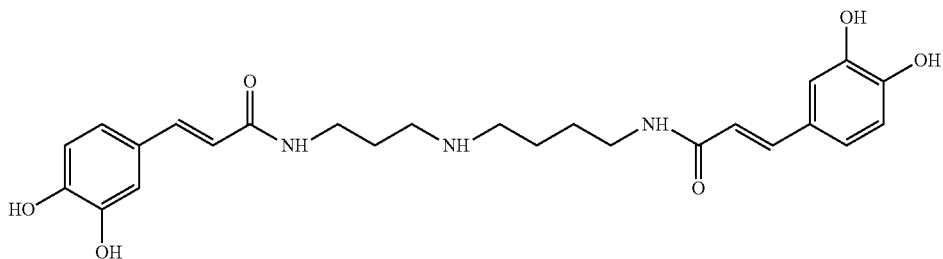 [SMILES: O=C(/C=C/c1ccc(O)c(O)c1)NCCCCNCCCNC(=O)/C=C/c1ccc(O)c(O)c1]

N1, N12-Bis(dihydrocaffeyl)spermine, having the formula:

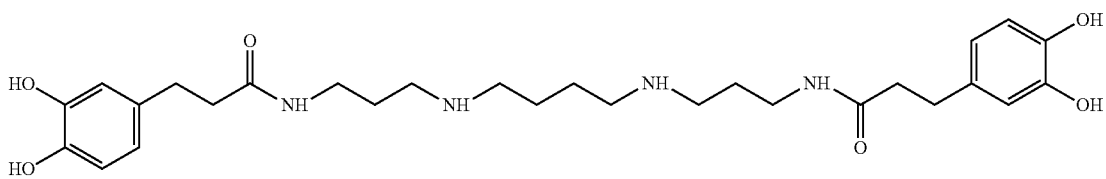 [SMILES: O=C(CCc1ccc(O)c(O)c1)NCCCNCCCCNCCCNC(=O)CCc1ccc(O)c(O)c1]

Fukinolic acid, having the formula:

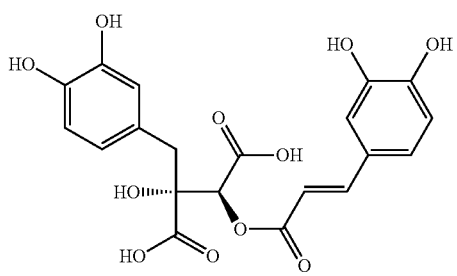 [SMILES: O=C(/C=C/c1ccc(O)c(O)c1)O[C@H](C(=O)O)[C@](O)(Cc1ccc(O)c(O)c1)C(=O)O]

N,N-Dicaffeyl-L-Lysine, having the formula:

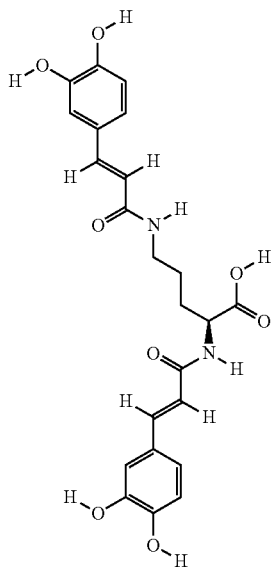 [SMILES: O=C(/C=C/c1ccc(O)c(O)c1)NCCC[C@H](NC(=O)/C=C/c1ccc(O)c(O)c1)C(=O)O]

1,2,3,4,6-Pentagalloylglucose, having the formula:

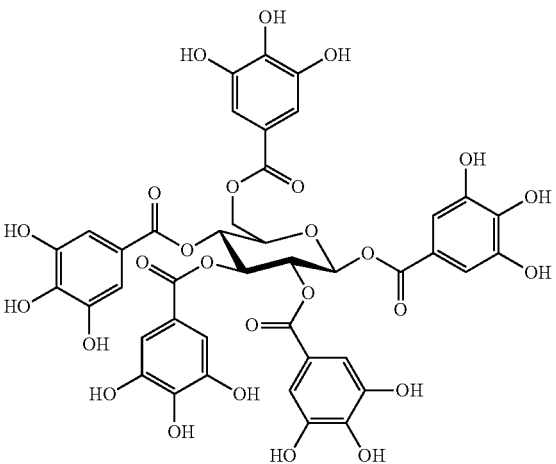

1,3,6-Trigalloylglucose, having the formula:

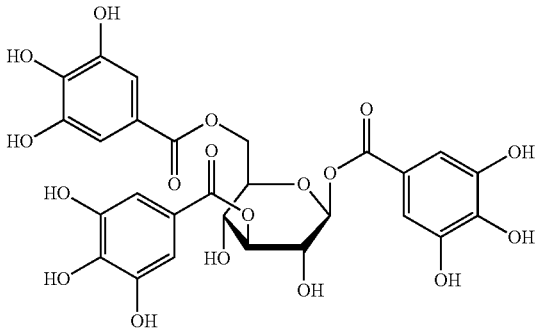

In one preferred embodiment of the invention, chicoric acid is used.

According to the invention, chicoric acid may be used in any of the isomeric forms thereof. It is notably possible to use, according to the invention, dicaffeyl-(2S, 3S)-(+)-tartaric acid, dicaffeyl-(2R,3R)-(−) tartaric acid, dicaffeyl-meso-tartaric acid, or mixtures thereof.

The expression "mixtures thereof", also used hereinafter in the application should be understood as meaning "any of the mixtures thereof in any proportions".

The expression "at least one compound (I)" means a compound having formula (I) or a mixture of at least 2 or 3 or 4 or more compounds having formula (I).

In some embodiments of the invention, the compounds having formula (I) as defined above may be in any one of the isomeric forms thereof. The term isomers denotes according to the invention, isomers in respect of structure and spatial arrangement. Preferably, the invention also relates to optically active forms (enantiomers, diastereoisomers and mixtures thereof).

The compounds having formula (I) may be in salt form. The salt forms of the compounds having formula (I) according to the invention are suitable for use in the phytosanitary field.

The compounds having formula (I) according to the invention may also be in solvated form.

The acceptable salts for phytosanitary applications of the compounds described in the present invention comprise conventional salts of said compounds such as alkaline or alkaline earth metal salts. The solvates of the compounds according to the invention comprise conventional solvates in phytosanitary applications, such as those formed during the final compound preparation step due to the presence of solvents.

The compounds having formula (I) suitable for use according to the invention, may be of natural or synthetic origin.

In one particular embodiment of the invention, at least one compound having formula (I) of plant origin is used.

According to the invention, the compound having formula (I), may be in more or less purified form, obtained by chemical synthesis, or purified from natural substances and notably plant substances. It may thus be in the form of one or a plurality of extracts of one or a plurality of natural substances containing same.

In one particular embodiment, chicoric acid or any one of the isomers of natural origin thereof is used as the compound having formula (I).

Chicoric acid (or any one of the isomers thereof) may be present in more or less purified form or in the form of one or a plurality of plant extracts containing same.

In particular, the chicoric acid may be isolated or purified from plants as described hereinafter. Methods for obtaining natural chicoric acid are described for example in Scarpati et al., "Chicoric Acid (Dicaffeyltartaric acid): Its isolation from Chicory and synthesis" Tetrahedron, 1958, Vol. 4, pp. 43-48 and in the application FR2904935.

The chicoric acid or derivatives thereof as defined in the present application may also be obtained by chemical synthesis, as described for example in the application WO03/029183, or by Lamidey et al. (2002) or Zhao et al. (1998) for obtaining synthetic chicoric acid.

Chicoric acid is notably found in numerous plant species belonging more particularly to the following families: Asteraceae, Lamiaceae, Fabaceae, Equisetaceae, Cymodoceaceae or Posidoniaceae or others, such as for example chicory (*Cichorium intybus*), lettuce (*Lactuca sativa*), echinacea (*Echinacea purpurea*), peanut (*Arachis hypogaea*), basil (*Ocimum basilicum*), horsetail (*Equisetum arvense*), dandelion (*Taraxacum officinalis*), plants of the violaceae family (notably *Viola brachyceras*), underwater plants, *Syringodium filiforme*, *Cymodocea nodosa* and posidonia (*Posidonia oceanica*). It is frequently the main phenolic compound of all the plant species and families cited above which may thus be used for the extraction and purification of this substance.

Advantageously, chicoric acid is obtained from plants belonging to the Asteraceae, Lamiaceae, Fabaceae, Equisetaceae, Cymodoceaceae or Posidoniaceae family, advantageously wild chicory (for example *Cichorium intybus*) or farmed chicory (for example Belgian endive or French endive), but also echinacea (such as *Echinacea purpurea*).

In the Asteraceae (or Compositae) family, chicoric acid may be obtained from plants of the genus: *Lactuca*, lettuce; *Cichorium*, chicory including Belgian endive (or French endive); *Cynara*, artichoke; *Taraxacum*, dandelion; *Echinacea*, *Echinacea* and *Lapsana*.

In the Lamiaceae (or Labiatae) family, chicoric acid may be obtained from plants of the genera: *Ocimum* (*Ocimum basilicum*, basil) and *Melissa* (*Melissa officinalis*, lemon balm).

In the Fabaceae (or Leguminose) family, chicoric acid may be obtained from Faboideae plants, notably *Arachis hypogaea*.

In the Cymodoceaceae family, chicoric acid may be obtained from plants of the genera *Syringodium*, more particularly of the species *Syringodium filiforme*, and *Cymodocea*, notably of the species *Cymodocea nodosa*.

In the Posidoniaceae family, chicoric acid may be obtained from plants of the genus *Posidonia*, such as posidonia (*Posidonia oceanica*). In the Equisetaceae family, chicoric acid may be obtained from: *Equisetum arvense*, horsetail.

The term phytosanitary use denotes according to the invention a use for preventing the establishment of pest insects or treating infested plants. In particular, the invention relates to uses for controlling plant pests. The term control denotes preventing infestations of the plants by said pests, repelling or eliminating said pests. A compound according to the invention may thus have a repellent or toxic action (paralyzing or lethal) according to the dose used and the pests targeted. As such, a compound having formula (I) according to the invention, and notably chicoric acid in any of the isomeric forms thereof, may be used according to the invention to exert at least one of the following effects: preventing, repelling or eliminating pest insects and in particular insects of the Aphidoidea and Phylloxeroidea superfamily.

The term "plants" denotes notably all plant species cultivated by humans, in particular those intended for food or for animal feed (cereals, fodder, vegetable, fruit crops, vines, etc.), and/or for the supply of wood for all purposes (heating, housing construction furniture, etc.) and/or ornamentation.

The term plant pests conventionally denotes any plant, animal or pathogenic agent species, strain or biotype that is harmful for plants or plant products. This definition notably covers insects and acarids, bacteria, fungi, viruses and parasitic plants.

The invention particularly relates to plant pest insects, notably phytophagous insects (particularly piercing-sucking insects) of the *Sternorrhyncha* sub-order, such as aphids and insects similar to aphids such as *phylloxera*, cochineals, whiteflies and *psylla*.

The invention notably relates to insects of the aphid superfamily, (Aphidoidea), which comprises the Oviparosiphidae, Pemphigidae, Anoeciidae, Hormaphididae, Tajmyraphididae, Mindaridae, Drepanosiphidae, Thelaxidae, Phloemyzidae, Greenideidae, Lachnidae and Aphididae family, and the Phylloxeroidea superfamily which comprises the Adelgidae, Mesozoicaphididae, Elektraphididae and Phylloxeridae families to which the species *Daktulosphaira vitifoliae* (formerly *Phylloxera vastatrix*) commonly known as Grapevine *Phylloxera* belongs.

Of the Aphidoidea and Phylloxeroidea superfamilies, the invention notably relates to the Aphididae families and the Adelgidae and Phylloxeridae families, very similar to aphididae. More particularly, the invention relates to the Aphididae family and the Phylloxeridae family, and notably in the latter family, *Daktulosphaira vitifoliae*.

In the Aphididae (commonly known as aphids) and Phylloxeridae families, the invention particularly relates to the species chosen in the group comprising *Myzus persicae* (green peach aphid), *Myzus varians* (peach-clematis aphid), *Myzus cerasi* (black cherry aphid), *Brachycaudus persicae* (black peach aphid), *Aphis pomi* (green apple aphid), *Brachycaudus hehchrysi* (leaf-curling plum aphid), *Hyalopterus pruni* (mealy plum aphid), *Dysaphis plantaginea* (rosy apple aphid), *Dysaphis pyri*, (pear bedstraw aphid), *Aphis gossypii* (cotton and melon aphid), *Acyrthosiphon pisum* (pea aphid), *Macrosiphvm euphorbiae* (pink and green potato aphid), *Aphis spiraecola* (*A. citricola*) (green citrus aphid), *Aphis fabae* (black bean aphid), *Rhopalosiphum maidis* (corn aphid), *Rhopalosiphum padi* (bird cherry-oat aphid), *Sitobion avenae* (English grain aphid), *Diuraphis noxia* (Russian wheat aphid), *Brevicoryne brassicae* (cabbage aphid), *Eriosoma lanigerum* (woolly apple aphid), *Nasonovia ribisnigri* (lettuce aphid), *Amphorophora idaei* (large raspberry aphid), *Toxoptera aurantii* (black citrus aphid and coffee aphid), *Elatobium abietinum* (green spruce aphid) and *Pemphigus bursarius* (lettuce aphid), for the Aphididae family; and *Daktulosphaira vitifoliae* commonly known as Grapevine *Phylloxera* for the Phylloxeridae family.

As such, the invention particularly relates to the species chosen in the group comprising *Myzus persicae* (green peach aphid), *Myzus varians* (peach-clematis aphid), *Myzus cerasi* (black cherry aphid), *Brachycaudus persicae* (black peach aphid), *Aphis pomi* (green apple aphid), *Brachycaudus hehchrysi* (leaf-curling plum aphid), *Hyalopterus pruni* (mealy plum aphid), *Dysaphis plantaginea* (rosy apple aphid), *Dysaphis pyri*, (pear bedstraw aphid), *Aphis gossypii* (cotton and melon aphid), *Acyrthosiphon pisum* (pea aphid), *Macrosiphvm euphorbiae* (pink and green potato aphid), *Aphis spiraecola* (*A. citricola*) (green citrus aphid), *Aphis fabae* (black bean aphid), *Rhopalosiphum maidis* (corn aphid), *Rhopalosiphum padi* (bird cherry-oat aphid), *Sitobion avenae* (English grain aphid), *Diuraphis noxia* (Russian wheat aphid), *Brevicoryne brassicae* (cabbage aphid), *Eriosoma lanigerum* (woolly apple aphid), *Nasonovia ribisnigri* (lettuce aphid), *Amphorophora idaei* (large raspberry aphid), *Toxoptera aurantii* (black citrus aphid and coffee aphid), *Elatobium abietinum* (green spruce aphid), *Pemphigus bursarius* (lettuce aphid), and *Daktulosphaira vitifoliae*.

In one particular embodiment, the invention relates to aphids chosen from the species *Myzus persicae* (green peach aphid), *Acyrthosiphon pisum* (pea aphid), *Aphis gossypii* (cotton and melon aphid), *Macrosiphum euphorbiae* (pink and green potato aphid), *Sitobion avenae* (English grain aphid).

In one embodiment of the invention, a compound according to the invention may be used in association with at least one further compound or substance chosen from nutrient, acaricidal, fungicidal, insecticidal substances or compounds.

In one particular embodiment, use will be made in association with at least one compound having formula (I) according to the invention, of at least one compound of natural origin, of plant or animal origin, suitable for use in the field of organic farming. Mention will notably be made of the compounds or substances chosen from: azadirachtin; gelatins; lecithin; laminarin, plant oils, notably essential oils such as peppermint and/or sweet orange, pine or caraway essential oils; pyrethrins; quassia, clove extract and fenugreek extract for the substances of animal or plant origin; spinosad, for the substances produced by microorganisms; along with iron phosphate, copper in the form of copper hydroxide, copper oxychloride, copper sulfate (tribasic), cuprous oxide, copper octanoate; ethylene; potassium salt of fatty acids; potassium alum (aluminum sulfate, kalinite); potassium bicarbonate, potassium phosphonate, acibenzolar-S-Methyl (ASM or BTH) and the functional analog thereof, salicylic acid; calcium polysulfide; paraffin oil; mineral oils; potassium permanganate; quartz sand; sulfur, pheromones, or further elicitor compounds approved for organic farming.

In some embodiments, active substances with insecticidal, and notably anti-aphid, activity (i.e. having a repellent or toxic activity against aphids) are preferred.

One compound having formula (I) according to the invention, and notably chicoric acid, may be used in a concentration, ranging from 0.06 to 5 mM, notably from 0.06 to 0.125 mM, from 0.06 to 0.120 mM, or from 0.125 to 5 mM, from 0.125 to 2 mM, from 0.125 to 1 mM, or from 0.125 to 0.5 mM.

In some embodiments, the compounds having formula (I) described above may be formulated in an effective quantity, in the form of a composition further containing at least one excipient, in particular in the form of a phytosanitary composition. Such a composition may also comprise at least one active ingredient other than a compound having formula (I) according to the invention.

The term effective quantity denotes a quantity of a compound having formula (I), or of a mixture of compounds having formula (I), suitable for obtaining the intended aim, i.e. that of preventing infestations of plants by pests, repelling or eliminating said pests.

As such, it was demonstrated in the invention, that a composition comprising a compound having formula (I) in an effective quantity would be suitable for repelling pest insects and particularly aphids. It was also demonstrated that increasing the concentration, of compound having formula (I) according to the invention, would be suitable for achieving a toxic effect against aphids and the larvae thereof.

In some embodiments of the invention, a phytosanitary composition comprises a concentration of a compound having formula (I) as described above, or of a mixture of compounds having formula (I), and preferably of chicoric acid, greater than or equal to 0.06 mM. In further embodiments, said composition will comprise a concentration of chicoric acid, or of any one of the derivatives thereof according to the invention, or of any one of the mixtures thereof, greater than 0.125 mM. It was thus demonstrated that a concentration between 0.06 mM (this lower limit being included within the range) and 0.125 mM was suitable for obtaining a repellent effect on plant pests and particularly on Aphididae. From 0.125 mM, a toxic effect, suitable for eliminating pests, is obtained.

Advantageously, a composition according to the invention will comprise concentrations of a compound having formula (I) or of a mixture of compounds having formula (I), ranging from 0.06 to 0.125 mM, in particular from 0.06 to 0.120 mM, or from 0.125 to 5 mM, from 0.125 to 2 mM, from 0.125 to 1 mM, or from 0.125 to 0.5 mM.

A composition comprising a concentration of a compound having formula (I) or a mixture of compound having formula (I) ranging from 0.06 mM to 0.125 (non-inclusive) mM, in particular from 0.06 mM to 0.12 mM will be preferentially used according to the invention for preventing or limiting the infestation of plants by pest insects.

A composition comprising a compound having formula (I) or of a mixture of compound having formula (I) greater than or equal to 0.125 mM will be preferentially used according to the invention for eliminating pest insects. Use will particularly be made of concentrations ranging from 0.125 to 5 mM, from 0.125 to 1 mM, from 0.125 to 0.5 mM, from 0.125 to 0.25 mM. In some embodiments, a concentration less than 1 mM will nonetheless be used.

In one particular embodiment, a phytosanitary composition according to the invention comprises at least chicoric acid, or any of the isomers thereof, chosen from dicaffeyl-(2S, 3S)-(+)-tartaric acid, dicaffeyl-(2R,3R)-(−) tartaric acid and dicaffeyl-meso-tartaric acid or any one of the mixtures thereof. Chicoric acid may also be in the form of a mixture with a further compound having formula (I) as defined above.

A composition according to the invention may also comprise at least one further active substance with a phytosanitary activity as described above. In particular, the composition may comprise at least one compound or a substance chosen from the group consisting of: azadirachtin; gelatins; lecithin; laminarin, plant oils, notably essential oils such as peppermint and/or sweet orange, pine or caraway essential oils; pyrethrins; quassia, clove extract and fenugreek extract for the substances of animal or plant origin; spinosad, for the substances produced by microorganisms; along with iron phosphate, copper in the form of copper hydroxide, copper oxychloride, copper sulfate (tribasic), cuprous oxide, copper octanoate; ethylene; potassium salt of fatty acids; potassium alum (aluminum sulfate, kalinite); potassium bicarbonate, potassium phosphonate, acibenzolar-S-Methyl (ASM or BTH) and the functional analog thereof, salicylic acid; calcium polysulfide; paraffin oil; mineral oils; potassium permanganate; quartz sand; sulfur, pheromones, or further elicitor compounds approved for organic farming.

In one particular embodiment, a phytosanitary composition, for example a composition for controlling insects of the aphid superfamily, and more particularly for controlling aphids and grapevine *phylloxera*, may comprise chicoric acid in association with at least one further compound or a further substance chosen from: pyrethrins; quassia, spinosad, copper in the form of copper hydroxide, copper oxychloride, copper sulfate (tribasic), cuprous oxide, sulfur, potassium bicarbonate, potassium phosphonate, acibenzolar-S-methyl, clove extract, fenugreek extract, essential oils, such as sweet orange, peppermint, pine or caraway essential oil, and pheromones.

In particular, the phytosanitary composition according to the invention may comprise chicoric acid in association with at least one further compound of natural origin having a phytosanitary activity, said at least one further compound being chosen from pyrethrins, essential oils, sulfur or copper in the form of copper hydroxide, copper oxychloride, copper sulfate (tribasic) or cuprous oxide.

In some embodiments, a phytosanitary composition according to the invention comprises a single active ingredient consisting of a compound having formula (I) or a mixture of compounds having formula (I). More particularly, a phytosanitary composition comprises chicoric acid in the form of any one of the isomers thereof or of the mixtures thereof as a single active ingredient.

The composition may be prepared according to various formulations suitable for phytosanitary uses, notably chosen from the group consisting of formulations of the following type: liquid intended for use without dilution (AL), powder intended for use without dilution (AP), encapsulated granule (CG), contact liquid or gel (CL), contact powder (CP), powdering powder (DP), emulsifiable concentrate (EC), emulsifiable granule (EG), oil type emulsion (EO), water type emulsion (EW), fine granule (FG), macrogranules (GG), emulsifiable gel (GL), powder for spraying (GP), granules (GR), grease (GS), water-soluble gel (GW), microemulsion (ME), microgranules (MG), water-dilutable concentrated suspension (OF), water-miscible suspension (OL), powder for dispersion in oil (OP), concentrated in gel or paste form (PC), sticks (for agri-pharmaceutical use) (PR), concentrated suspension (SC), suspoemulsion (SE), water-soluble granules (DG), soluble concentrate (SL), film-forming oil (SO), water-soluble powder (SP), water-soluble tablets (ST), tablets (TB), water-dispersible granules (WG), wettable powder (WP), water-dispersible tablets (WT)—the code consisting of two capital letters corresponding to the international codes for phytosanitary formulations (Manuel of Development and use of FAO specifications for plant protection Products, FAO, 5th edition, 1999, based on the "Catalogue of pesticides formulations types and international coding system", CIFAP, Technical monograph No. 2, 32nd edition, 1989).

According to the formulation adopted, a phytosanitary composition according to the invention will comprise one or a plurality of excipient(s) intended to present the active ingredient(s) (compound according to the invention and optionally at least one further compound or a further substance having phytosanitary activity) in a stable form and suitable for the application thereof, by adding thereto excipients intended to increase and promote the action thereof.

The formulation of a composition according to the invention notably makes it possible to ensure optimal efficacy/efficiency of the active ingredient(s). As such, in order to limit the dispersion thereof in the environment and the dosage required, a composition may comprise wetting agents. These agents increase the spread of the pesticide on the treated surface and reduce the angle of contact of the droplets with the plant (or animal) substrate, with two consequences: superior adhesion and a greater contact and action surface area. The formulation may also increase the biological efficacy/efficiency of the active molecule with additives delaying the degradation thereof and thus prolonging the period of action thereof. Conversely, further additives may accelerate the elimination thereof by the plants to be protected or in the soil.

Adding certain excipients may also be intended to limit the risks of poisoning for the handler: so as to obtain a minimal toxicity by contact and inhalation, by preventing accidental ingestion, adjuvants chosen from dyes, repellents, antidotes or emetics may be added in a composition according the invention.

In order to ensure the profitability of the active ingredient(s), the solvent(s) used if applicable will be generally inexpensive and readily available. Additional excipients may be used for increasing the shelf-life and/or preventing spreading apparatus corrosion.

A composition according to the invention may thus comprise in a non-limiting manner and by way of example at least one excipient chosen from: solvents, surfactants, adhesives, emulsifying agents, stabilizers, photoprotective agents, antiperspirants, dyes, repellent substances, viscosity-modifying agents, anti-foaming agents, notably silicone anti-foaming agents, anti-bounce agents, anti-leaching agents, complexing agents, corrosion inhibitors, inert fillers, notably mineral fillers, anti-freeze agents, emetics and in some cases antidotes.

In one particular embodiment, a composition according to the invention comprises at least one excipient chosen from the group consisting of corrosion inhibitors, anti-freeze agents, emetics, etc.

The present invention also relates to a phytosanitary treatment method and notably a method for controlling plant pests, in particular a method for controlling plant pest insects and more particularly a method for controlling aphids, as mentioned above.

Such a method according to the invention comprises at least one step consisting of applying at least one compound having formula (I), preferably at least chicoric acid, or a composition containing same and as described above, on aphids, or on plants or on parts of plants infested with pests or potential pests.

The treatment method according to the invention generally uses doses of active substance ranging from 0.1 to 10,000 g/ha, preferably from 10 to 2000 g/ha, for example from 50 to 1000 g/ha. These doses may be may be adapted according to the composition according to the invention and the formulation which is used and according to the weather conditions, any resistance phenomena or other natural factors, the nature of the treatment or the degree of infestation, and according to the plants or sites to be treated.

EXAMPLES

Procedure:

a) Analysis of repellent effect: the method used is that developed by Yvan Rahbé (Rahbé & Febvay (1993) Entomologia Experimentalis et Applicata 67: 149-160; Chen (1996) Thesis submitted to Institut National des Sciences Appliquées, Lyon, France: 158 p) within the scope of research on the chemical determinants of the resistance of plants to various species of aphids (*Aphis gossypii, Acyrthosiphon pisum*), and adapted to the green aphid *Myzus persicae*.

The objective is to evaluate the attractive or repellent nature of a candidate molecule, at different concentrations, either with respect to control base medium (dose "0"), or with respect to another substance. The base medium used, referred to as Ap3, an artificial medium developed for breeding the pea aphid, *Acyrthosiphon pisum*, and reproducing the amino acid composition thereof, (Febvay et al. (1999) *Fate of dietary sucrose and neosynthesis of amino acids in the pea aphid, Acyrthosiphon pisum, reared on different diets*. Journal of Experimental Biology, 1999, 202 (19): 2639-2652; Febvay et al. (1988) Canadian Journal of Zoology 66: 2149-2453) is also suitable for the growth of *Myzus persicae*. This base medium is supplemented or not with chicoric acid (dicaffeyl tartaric acid) or caftaric acid (monocaffeyl tartaric acid). The behavior of choice of the aphid, placed in the presence of both media, is studied in a closed system where the insect has no alternative to feed other than choosing one of the two media.

The medium (35 μl) is poured between two Parafilm® membranes stretched onto an Eppendorf® cone. On a rack comprising 6 experimental cages, a control medium is arranged opposite a medium tested on each cage. The repetitions of the same mode (control medium or test medium) are arranged in alternation along the rack, to prevent any systematic bias during aphid deposition. Six aphid larvae (second or third stage) are deposited at the end of the day in each of the cages of a rack. The racks are then introduced into a black box placed in a climatic chamber at 19° C. for 15 hours. This passage in darkness makes it possible to stabilize the larva fixation more rapidly. The following morning, the number of aphids fixed on each medium is then recorded. The tests are performed routinely on 24 repetitions of choice (4 racks each comprising 6 cages). A phagostimulation index, representing the degree of appetence of the test medium for the aphid, is calculated as follows:

Phagostimulation index=(No. test−No. control)/Total No., where:

No. test=Number of aphids fixed on the test medium,

No. control=Number of aphids fixed on the control medium,

Total No.=Total number of aphids fixed.

By construction, the value of the index is between −1 and 1. A negative index indicates that the test medium is repellent with respect to the control medium, and a positive index indicates that the test medium is attractive. The hypothesis that the effect of the test medium is identical to that of the control medium is examined using the Wilcoxon rank test.

The chicoric acid and caftaric acid are of commercial origin (Sigma-Aldrich, France). The content and stability of the dissolved molecules are tested by HPLC after dissolving the molecules in Ap3 medium, at the start and end of testing.

b) Measurement of the toxicity of chicoric acid or caftaric acid on larval growth of the green peach aphid (*Myzus persicae*) and the pea aphid (*Acyrthosiphon pisum*)

The objective is to quantify the toxic effect of chicoric acid or caftaric acid on the aphid for the period of larval growth thereof, i.e. 8 to 10 days for *Myzus persicae* and *Acyrthosiphon pisum* at 19° C. The molecule is added at different concentrations to the Ap3 control nutrient medium. The dose "0" corresponds to Ap3 medium alone.

The medium (75 μl) is poured between two UV-sterilized Parafilm® stretched onto a cylindrical PVC support (h=1.5 cm, d=2 cm), under sterile conditions.

On the Day D0, 20 neonate larvae are deposited inside the cylinder, which is then turned over and applied to a square of Parafilm©. The dishes are placed in filtered light (16 hours day/8 hours night) and in a chamber at 19° C. The fixation percentage is recorded after 1 hour as a short-term phagostimulation indicator and to check that no anomaly occurred during aphid deposition. The larval mortality is recorded daily at the end of the day. On the day D+3, the larvae are sampled and divided into two new dishes. On the day of the imaginal moult thereof, the aphids having reached the adult aptera stage are deposited successively on a precision balance (d=0.01 mg) and the cumulative weights are recorded for each concentration of each of the two molecules tested. The individual weights are calculated subsequently. The effects of the same molecule at all the concentrations and the effects of the control medium are evaluated simultaneously during the same test. The tests are conducted routinely on 3 repetitions.

Results:

a) Analysis of repellent effect (FIGS. 1A and 1B).

The results obtained demonstrate a significant repellent effect of chicoric acid and a lack of effect of caftaric acid merely comprising a caffeyl group.

Chicoric acid, or dicaffeyl tartaric acid, displays a highly significant repellent effect from the dose of 62.5 μM. On the other hand, caftaric acid does not display a repellent effect for any of the doses tested.

b) Toxic effect of chicoric acid or caftaric acid on larval mortality (FIGS. 2 and 3).

A very pronounced effect of chicoric acid on larval mortality of the aphid *Myzus persicae* is observed (FIG. 2), which progressively increases during insect growth. The mortality also increases with the concentration, to attain practically 80% from 0.125 mM and 100% from 0.25 mM. On the other hand, the mortality of *myzus persicae* never exceeds 10% in the presence of caftaric acid (including at the highest concentrations).

A very pronounced toxic effect of chicoric acid on the pea aphid (*Acyrthosiphon pisum*) is also observed (FIG. 3) with a very significant effect (p<0.001) from a dose of 0.5 mM suitable for attaining a mortality greater than 80% and ranging up to 100%.

The invention claimed is:

1. A method for controlling insects of the Aphidoidea and Phylloxeroidea superfamily comprising applying to said insects or plants a compound having formula (I)

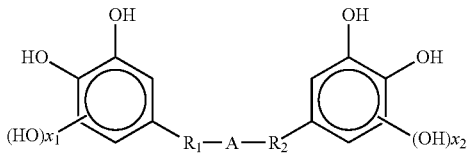

wherein,
$x_1$ and $x_2$ are each independently=0 or 1;
—$R_1$— represents a group chosen from

$R_2$— represents a group chosen from

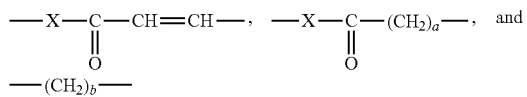

wherein for —$R_1$— and —$R_2$—:
—X— represents O or N,
a=0, 1, or 2
b=1, 2 or 3;
-A- represents a mono-saccharide, a di-saccharide or a group chosen from:

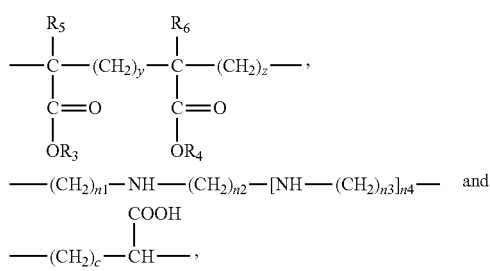

wherein
y and z are each independently equal to 0, 1, 2, 3 or 4
$R_3$ and $R_4$ each represent independently H or a $C_1$-$C_3$ alkyl
$R_5$ and $R_6$ each represent independently H, OH or the group

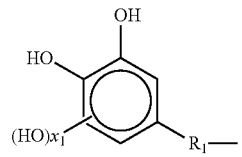

where —$R_1$— chosen between

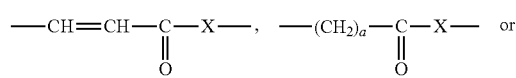

and —$R_2$— chosen between

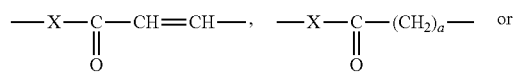

or
$n_1$, $n_2$, $n_3$ are each independently equal to 1, 2, 3, or 4 and $n_4$=0 or 1
c=2, 3 or 4.

2. The method according to claim 1, wherein said compound having formula (I),
—$R_1$— represents a group chosen from:

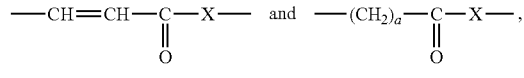

wherein —X— represents O and a=1 or 2, and
—$R_2$— represents a group chosen from:

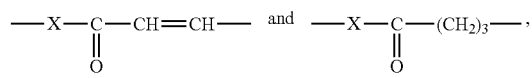

wherein —X— represents O and a=1 or 2;
-A- represents the group

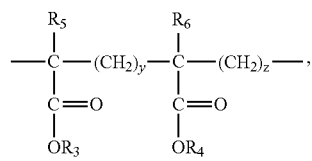

wherein y and z are each equal to 0 or 1, and $R_3$, $R_4$, $R_5$ and $R_6$ are each H.

3. The method according to claim 2, wherein said compound having formula (I) is chicoric acid.

4. The method according to claim 3, wherein the compound having formula (I) is chicoric acid and is formulated in a phytosanitary composition at a concentration greater than or equal to 0.06 mM.

5. The method according to claim 3, wherein the chicoric acid is at a concentration greater than 0.125 mM.

6. The method according to claim 1, wherein said compound having formula (I),
—$R_1$— represents a group chosen from

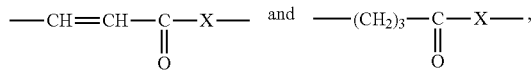

wherein —X— represents N and a=1 or 2; and
—$R_2$— represents a group chosen from

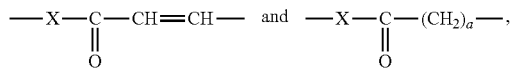

wherein —X— represents N and a=1 or 2; and
A represents the group —$(CH_2)_{n1}$—NH—$(CH_2)_{n2}$—[NH—$(CH_2)_{n3}]_{n4}$—, wherein $n_1$, $n_2$, $n_3$ are each independently equal to 1, 2, 3, or 4 and $n_4$=0 or 1.

7. The method according to claim 1, wherein the compound having formula (I) is associated with at least one second substance having a phytosanitary activity and/or a nutrient substance.

8. The method according to claim 1, wherein the insects belonging to the Aphidoidea and Phylloxeroidea superfamily are chosen from the Aphididae and Phylloxeridae families.

9. The method according to claim 8, wherein the insects are selected from the group consisting of: *Myzus persicae* (green peach aphid), *Myzus varians* (peach-clematis aphid), *Myzus cerasi* (black cherry aphid), *Brachycaudus persicae* (black peach aphid), *Aphis pomi* (green apple aphid), *Brachycaudus helichrysi* (leaf-curling plum aphid), *Hyalopterus pruni* (mealy plum aphid), *Dysaphis plantaginea* (rosy apple aphid), *Dysaphis pyri*, (pear bedstraw aphid), *Aphisgossyipii* (cotton and melon aphid), *Acyrthosiphon pisum* (pea aphid), *Macrosiphum euphorbiae* (pink and green potato aphid), *Aphis spiraecola* (*A. citricola*) (green citrus aphid), *Aphis fabae* (black bean aphid), *Rhopalosiphum maidis* (corn aphid), *Rhopalosiphum padi* (bird cherry-oat aphid), *Sitobionavenae* (English grain aphid), *Diuraphis noxia* (Russian wheat aphid), *Brevicoryne brassicae* (cabbage aphid), *Eriosoma lanigerum* (woolly apple aphid), *Nasonovia ribisnigri* (lettuce aphid), *Amphorophora idaei* (large raspberry aphid), *Toxoptera aurantii* (black citrus aphid and coffee aphid), *Elatobium abietinum* (green spruce aphid) and *Pemphigus bursarius* (lettuce aphid), and *Daktulosphairavitifoliae* (grapevine *phylloxera*).

10. The method according to claim 9, wherein the aphid is from the group consisting of *Myzus persicae* (green peach aphid), *Acyrthosiphon pisum* (pea aphid), *Aphis gossypii* (cotton and melon aphid), *Macrosiphum euphorbiae* (pink and green potato aphid) and *Sitobion avenae*(English grain aphid).

11. A phytosanitary composition comprising chicoric acid in a concentration ranging from 0.06 to 5 mM, at least one further active substance having a phytosanitary activity, and at least one excipient suitable for phytosanitary use.

12. A phytosanitary treatment method, comprising a step consisting of applying at least one compound having formula (I) or a composition containing same, on aphids, or on a site infested with aphids or on a site liable to be infested by aphids.

* * * * *